United States Patent [19]
Challis et al.

[11] Patent Number: 5,672,406
[45] Date of Patent: Sep. 30, 1997

[54] MATERIAL HAVING A THERMALLY EXPANDABLE PASSAGE

[75] Inventors: Anthony Arthur Leonard Challis, Langport; Michael John Bevis, Uxbridge, both of England

[73] Assignee: British Technology Group Limited, London, England

[21] Appl. No.: 122,418

[22] PCT Filed: Mar. 24, 1992

[86] PCT No.: PCT/GB92/00537

§ 371 Date: Jan. 21, 1994

§ 102(e) Date: Jan. 21, 1994

[87] PCT Pub. No.: WO92/16434

PCT Pub. Date: Oct. 1, 1992

[30] Foreign Application Priority Data

Mar. 25, 1991 [GB] United Kingdom ............... 9106317

[51] Int. Cl.[6] .................... B32B 3/24; B65D 65/00
[52] U.S. Cl. ................... 428/136; 428/131; 428/132; 428/134; 428/135; 428/137; 428/913; 426/326; 426/324; 426/316; 426/415; 426/118; 383/102; 383/103
[58] Field of Search ............... 428/131, 132, 428/134, 135, 136, 137, 913; 426/326, 324, 316, 415, 118; 383/102, 103

[56] References Cited

U.S. PATENT DOCUMENTS

| | | | |
|---|---|---|---|
| 3,026,209 | 3/1962 | Wiblack et al. | 426/124 |
| 3,040,966 | 6/1962 | Crane | 428/136 |
| 3,097,787 | 7/1963 | Schur | 428/132 |
| 3,245,606 | 4/1966 | Crane | 229/53 |

(List continued on next page.)

FOREIGN PATENT DOCUMENTS

| | | |
|---|---|---|
| 819635 | 9/1959 | European Pat. Off. . |
| 1084550 | 9/1967 | European Pat. Off. . |
| 1269025 | 3/1972 | European Pat. Off. . |
| 1280631 | 7/1972 | European Pat. Off. . |

(List continued on next page.)

OTHER PUBLICATIONS

Printout Abstracts "Freshhold", Ventflex, Hercules and DRG Ventflex.

Process Industry Journa Jul./Aug. 1989 p. 9 "Creating the right atmosphere".

Independent "Packing discovery prolongs shelf–like" Jun. 1989.

*Primary Examiner*—William Watkins
*Attorney, Agent, or Firm*—Cushman, Darby & Cushman IP Group of Pillsbury Madison & Sutro LLP

[57] ABSTRACT

A bilayer laminated material has a gas permeability increasing greatly with temperature, achieved by cutting a star-shaped hole in it when it is relaxed and flat. On warming, the leaves between the radial cuts curl and disproportionately increase the hole size. Such a material, if flat at 5° C. and wide open at 20° C., is useful for packaging vegetable produce.

25 Claims, 2 Drawing Sheets

U.S. PATENT DOCUMENTS

| | | | |
|---|---|---|---|
| 3,795,749 | 3/1974 | Cummin et al. | 426/316 |
| 4,141,487 | 2/1979 | Faust et al. | 229/43 |
| 4,419,373 | 12/1983 | Oppermann | 426/234 |
| 4,497,431 | 2/1985 | Fay | 426/113 |
| 4,503,561 | 3/1985 | Bruno | 383/102 |
| 4,530,440 | 7/1985 | Leong | 426/118 |
| 4,541,426 | 9/1985 | Webster | 128/156 |
| 4,740,378 | 4/1988 | Jameson | 426/419 |
| 4,805,398 | 2/1989 | Jourdain et al. | 415/116 |
| 4,886,372 | 12/1989 | Greengrass et al. | 383/100 |
| 4,944,187 | 7/1990 | Frick et al. | 73/718 |
| 5,053,594 | 10/1991 | Thota et al. | 426/118 |
| 5,114,766 | 5/1992 | Jacques | 428/35.7 |
| 5,254,354 | 10/1993 | Stewart | 426/106 |
| 5,330,811 | 7/1994 | Buchalter | 428/40 |

FOREIGN PATENT DOCUMENTS

| | | |
|---|---|---|
| 1305829 | 2/1973 | European Pat. Off. . |
| 86057 | 8/1983 | European Pat. Off. . |
| 155035 | 9/1985 | European Pat. Off. . |
| 0218419 | 4/1987 | European Pat. Off. . |
| 270764 | 6/1988 | European Pat. Off. . |
| 271268 | 6/1988 | European Pat. Off. . |
| 282180 | 9/1988 | European Pat. Off. . |
| 3122194 | 1/1983 | Germany . |
| 3122194 | 5/1983 | Germany . |
| 2124339 | 2/1984 | United Kingdom . |
| 2141688 | 1/1985 | United Kingdom . |
| 2200618 | 6/1989 | United Kingdom . |

1

MATERIAL HAVING A THERMALLY EXPANDABLE PASSAGE

BACKGROUND OF THE INVENTION

The present invention relates to a material having a passage therethrough. (The passage may be completely closable.) Such material has a wide variety of applications. For illustration, the invention will be described with reference to one such application, namely packaging of edible produce, in particular to maintain it in a preservative atmosphere, bearing in mind that the requirements can vary with temperature.

All harvested vegetables, flowers and fruits continue to respire, absorbing oxygen and emitting carbon dioxide. A number of parallel biological paths are involved leading to loss of weight (although loss of water is usually the main cause of weight loss), some heat production, loss or change of flavour, change of texture, and discoloration of outer surfaces or cut surfaces or in the body of the product. The growth and excretions of micro-organisms present at harvesting can produce other changes. Virtually all these changes are deleterious to the acceptability of the product to the consumer.

Respiration increases with increasing temperature. The main method of increasing storage life is therefore to hold the product at lowered temperatures, often a little above 0° C. However some products (e.g. runner beans, cucumbers, green peppers, tomatoes, bananas) cannot be stored below 5°–11° C. Respiration rates show a wide range, broccoli being nearly $10^2$ times as fast as onions or potatoes. Values also vary with variety within a given species, cropping and harvesting methods used, year of crop and degree of ripeness.

It might be thought that the respiration rate (in particular the carbon dioxide production rate) could be sharply reduced by lowering the concentration of oxygen. However below 2–3% (depending on product) anaerobic processes begin, due to both the product and its accompanying micro-organisms. These, usually, produce rapid and unacceptable tainting of flavour. Alcohol production by yeasts often predominates while aldehydes are often the main cause of unacceptability.

If a product is wrapped in a sealed impermeable packaging system then even a modest respirer such as tomatoes soon lowers the oxygen concentration to anaerobic conditions. Ripening of tomatoes is completely inhibited and does not resume when the package is opened and many of the fruits develop rots or suffer fungal attack. (An atmosphere of 6% oxygen retards ripening, which however recommences on opening to air, with no adverse effects on eating quality.) To overcome this rot problem, it is known to pass such a sealed impermeable pack (preferably after a short period of storage and temperature reduction, to allow the oxygen concentration to drop rapidly), under an adjustable mechanical 'pecking' head which punches in the necessary holes, e.g. typically three holes of 0.4 mm$^2$ per pack. Changing their diameter or number provides easy adjustment for product type, variety type, weight and expected downstream conditions before consumption etc—always provided the basic knowledge is available. However, by itself, this has been found to give inadequate variation with temperature.

An alternative approach to this problem has been to devise selectively permeable materials which can be used as panels in gas-impermeable wrapping materials for fresh fruit, vegetables or flowers. These panels can be of a microporous material having greater $CO_2$ permeability than $O_2$ permeability, and it has been proposed to use that area of material as will transmit oxygen at the same rate as the packaged contents will consume it. However, this presupposes a certain temperature of storage, as oxygen consumption of produce increases much more sharply with temperature than does the oxygen transmissibility of the material. At accidentally high temperatures, therefore, the oxygen within such a wrapping will be consumed much faster than it can be replenished, leading to anaerobic conditions and their drawbacks as already described.

It is known that high carbon dioxide concentrations inhibit micro-organisms so that it could be advantageous to maintain such levels for packaged fruit and vegetables which tolerate such concentrations.

Regarding water vapour, the optimum requirement seems to be a relative humidity of just under 100%, but with no liquid water present, both from appearance of the pack and for the discouragement of fungal growths.

It would therefore be desirable to devise a material having a passage therethrough, which passage changes in size with temperature at a higher rate than the thermal coefficient of expansion of the material, over at least a certain temperature range, e.g. increasing as temperature rises from −5° C. or 0° C. to 20° C.

SUMMARY OF THE INVENTION

According to the present invention, a flexible material is asymmetrically laminated from at least two layers having different coefficients of thermal expansion, the material having a non-straight slit, at least one and preferably at least two layers (preferably adjacent) being of plastics. At least one layer may be a metal foil adhered to a plastics layer or may be a layer of metal deposited directly thereonto, by any suitable metallisation method. Note that the two layers contribute synergistically to the variation of aperture size with temperature. The asymmetry is such that the material tends to curl as its temperature moves away from a so-called lie-flat point. The lie-flat point preferably is within the range −5° to 20° C., more preferably within the range 0° C. to 20° C. The lie-flat point is often (but not always) the temperature of the layers at the time they were laminated. The asymmetry can thus reside in the identities of the layers or in their respective thicknesses or in both. As to thicknesses, it is preferred that the layers (preferably all, but most or some will do, especially if it is the two outside ones) of a material have thicknesses in proportion to the inverse cube root of their respective Young's moduli, to within a reasonable approximation.

In one aspect, the slit has the form of two or more slots radiating from a junction, at least one pair of adjacent slots preferably forming an angle of at most 90° (and more preferably at least two pairs of adjacent slots form an angle of at most 60°). The junction may be an aperture of sensible size. Some or all of the slit may be produced by laser.

The aperture may be constant or adjustable ranging from one hole (which would typically be from 0.05 to 1.0 mm$^2$ for most retail packs and products), to many holes of few microns diameter.

The gas permeability of the apertured laminate should increase at least threefold from 5° C. to 20° C. This would make it especially suitable to be used in a package (e.g. comprising all or part of the wrapping) for respiring edible produce.

A packaging film has to fulfill many demands, e.g. of strength, toughness, often clarity, or transparency sealability, printability, ability of the inner surface to disguise or spread water droplets, and finally price. To achieve this while offering a controlled and specific series of permeabilities with a prescribed temperature variation is to steer between Scylla and Charybdis while gazing on Medusa. Therefore to instances where a material according to the invention cannot be used as the packaging film itself, there is merit in the concept of a small area of material according to the invention in a package or other container made otherwise from a conventional commercial packaging film. The small area needs no transparency etc, only a suitable permeability and strength.

The invention may be realised for packaging edible produce and other uses (exemplified later) by films or membranes of plastics, polymers or other materials, and/or of stouter sheets such as of metal foil or sheet and/or of semi-rigid sheets of plastics or polymers, which themselves may be loaded with metal powder. The materials are preferably inert (especially, dimensionally inert) to moisture, in particular do not swell when humid or wet, and may indeed be hydrophobic. Two-layer laminates are preferred, especially where one layer is polyester and/or the other is polyolefin (usually polyethylene). Alternatively, polyamide, cellulosic or polyethylene terephthalate film can be paired with low density polyolefin (e.g. polyethylene) film, which may be metallised, or with ethyl vinyl acetate film. It will be self-evident that the laminate must be asymmetrical; thus a symmetrically laminated material of layers of polymers A, B, C, B, A where the A thicknesses were equal to each other and the B thicknesses were equal to each other would be thermally inert. The thermal coefficients of expansion of the materials should be very different.

BRIEF DESCRIPTION OF THE DRAWINGS

The invention will now be described by way of example with reference to the accompanying drawings, in which.

DESCRIPTION OF THE PREFERRED EMBODIMENT

Figure 1:
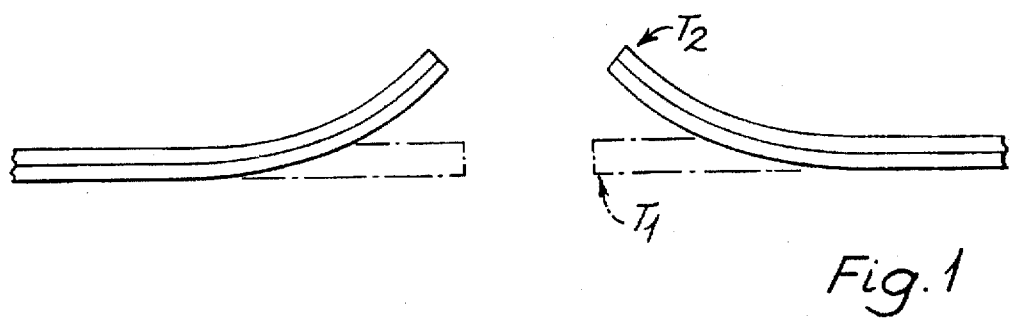
FIG. 1 shows in cross section and FIG. 2 in plan a material according to the invention, having a temperature dependent variable-shape hole.
Figure 2:
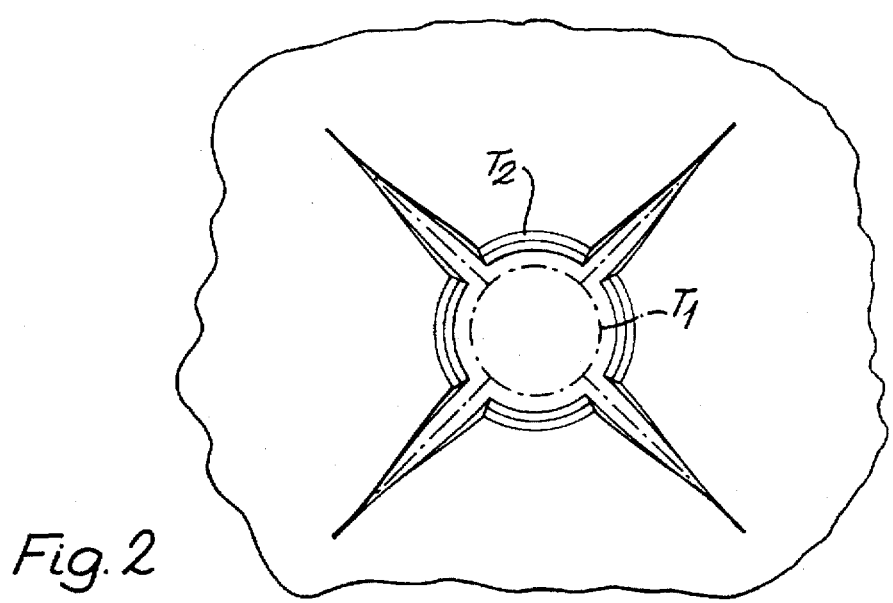

Consider FIGS. 1 and 2. The system uses a two layer film, of two polymers with fairly widely different temperature coefficients of expansion, for example polyethylene and polyester. Each film is made separately by blowing or calendering and annealing for flatness, and then the films are stuck together by a thin layer of flexible elastomeric adhesive such as neoprene while held flat at a temperature $T_1$ (e.g. 0° C.) being the lowest storage temperature required for the product. An alternative adhesive is a thin layer of an aqueous emulsion of a modified acrylic adhesive such as 3M (trade mark) 3565. Solvent-based adhesives can be used for strength. Another successful two-layer film pairing is 12-micron biaxially oriented polyethylene terephthalate film stuck to 36-micron low-density polyethylene film plasma-treated on one face to improve adhesion with a 12 micron (wet) (=6–8 micron when dry) layer of 3M 3565 adhesive, the whole consolidated by a rubber roller. In general, as remarked previously, it is preferred that the lie-flat temperature should be somewhere in the range −5° to 20° C., usually 0° to 20° C. Sample films made at 4° C., 8° C. and 20° C. respectively all curled up to form a roll (polyethylene outwards) of under 1 cm diameter when subjected to a 20° C. temperature rise. In this film a "pecked hole" is made of a suitable size (e.g. ¼ mm²) for $T_1$. Radiating at equal angles apart from the hole are four (possibly 6 or 8) cuts each 3 mm long in the film. As the temperature rises from $T_1$ to $T_2$ the differential expansion of the two film components causes the radial segments between the cuts to curl, as in a bimetallic strip, and increases the area of the total void (i.e. both the hole itself and opening of the radial cuts). As an alternative to a pecked hole, a material of high inherent permeability could be used; for example, a 25 micron film of ethylene-vinyl acetate transmits 12 litres of oxygen per m² per day per atmosphere overpressure at 23° C. at 0% relative humidity.

From the foregoing, it will be seen that there are two possibilities of incorporating such holes. First is to use the bicomponent film for the whole pack. (Already multicomponent packaging film is commonplace. The outer layer often, for example, provides good gloss and printability, the inner layer provides easy sealing and the ability to spread and disguise condensed water. A cheap polymer as the central component can provide the strength and handling properties, while the barrier properties are the sum of the performance of the individual layers.) An alternative Is to use an existing standard barrier pack with a (say) 1 cm² opening covered by a stuck or ultrasonically welded piece or patch of bicomponent film containing the temperature-dependent hole. The hole could be pecked at this stage (rather than earlier), e.g. mechanically or by laser cutters. The patches could be dispensed from a tear-off roll. This would use less of the specialist polymer and would lend itself to further elaboration, e.g. a cage to protect the curl of the radial segments or a protective layer peeled off before use. Pre-pecked stick-on patches are illustrated later. A useful step would be to combine the patch with the package label (showing the normal information such as contents, weight, 'sell by' date, bar code and price) to ensure that the correct grade of patch is applied on a pack. For its own protection and efficacy, the curl is preferably inwards into the pack.

In laminar flow through capillaries, the mass flow rate is proportional to the gas density divided by the viscosity (which changes by about 10% over the temperature range 5°–20° C.). However the mass flow rate is also proportional to the fourth power of the radius of the flow path. Using differential co-efficients of expansion of $1 \times 10^{-4}$° C. (e.g. nylon/polyethylene), it should be possible to achieve the desirable fourfold increase of gas flow over the 15° C. temperature range.

Bilayers can alternatively be made using a multiple extruder. With appropriate choice of materials and fabrication conditions, such a material can surprisingly be induced to lie flat at some convenient temperature other than the temperature of fabrication. Normally however the bilayer would be assembled and cut, flat, at the temperature where minimum gas permeability is wanted. This temperature is called the lie-flat temperature. For (for example) tropical whole fruit such as bananas and mangoes, this would be 10°–15° C., with the gas flow increasing up to say 25° C. but not opening in reverse (see later) below 10° C. For vegetables, the respective temperatures would be 2°–5° C. and 20° C.; accidental freezing is unlikely, and a reverse-opening preventer can sometimes be dispensed with.

Figure 3:
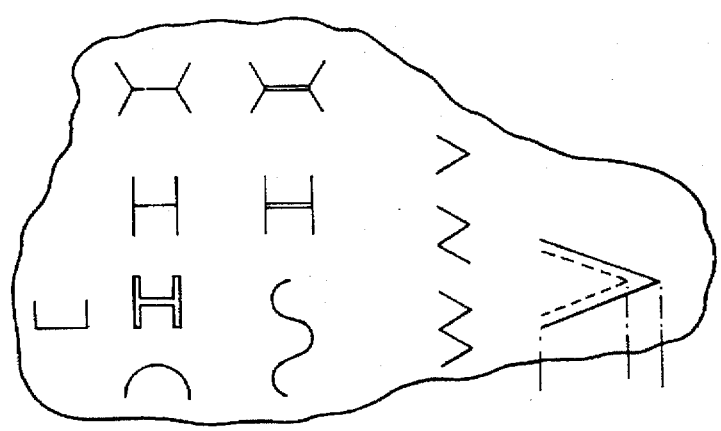
FIG. 3 shows in plan a material according to the invention with different apertures.

Turning to FIG. 3, a selection of alternative shapes of hole is illustrated, such as V, H, S and C. They all have in common that they are not straight and therefore, when the material curls, open disproportionately, as is desired, but to different extents as geometrically determined by the height/width ratio of the H, the vertex angle of V, etc. This gives a choice of hole size/temperature profiles, from which the most suitable for a particular application may be selected. The holes may be mechanically cut by a press knife mounted in a punch or may be formed by laser (e.g. excimer laser ablation), by which it is less likely than with mechanical cutting that the hole will have ragged cuts that would tangle and interfere with each other when supposed to open. In practice, mechanical cutting is adequate except for oblique cuts, described later. Some parts of the hole may be cut out more extensively, e.g. the crossbar of the H, if the hole is required to remain of at least a certain size whatever the temperature. With laser cutting, the hole at the lie-flat temperature can have effectively zero size. Any residual gas transmission which may be required for a particular application at the lie-flat temperature in a material where the passages are then of zero size may be achieved if the material itself has an appropriate inherent permeability.

Figure 4:
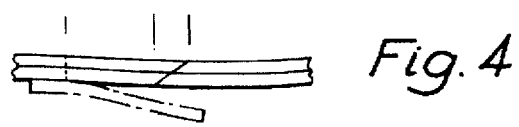
FIG. 4 shows in cross-section one of the apertures of FIG. 3, taken on a plane through the vertex of that aperture (the V-shaped one).

FIG. 4 shows in cross-section the V hole of FIG. 3. It will be seen that the cut is oblique at the vertex of the V. (Oblique cuts are most easily made by laser). Consider a temperature excursion below the set point of the laminate, which tends then to curl in the direction of the arrow. The oblique cut prevents it from opening. Another way of preventing the hole from opening during downward temperature excursions is to provide a backing flap (which may be selective as between $O_2$ and $CO_2$ or other gases) shown in chain-dotted lines on FIG. 4. Possible materials for the backing flap include a fine polymeric net, a mesh, an open-structured non-woven polymeric fibre fabric or an open weave woven polymeric fibre fabric. It may be seamed to the material along one edge as shown in FIG. 4 or along any fraction(s) or all of its perimeter. Sometimes it will be desirable to prevent biological contamination through the material. In such a case, the backing flap would be seamed all round and could be of a microporous sheet or laminate with pore size <5 μm, for example.

Figure 5:
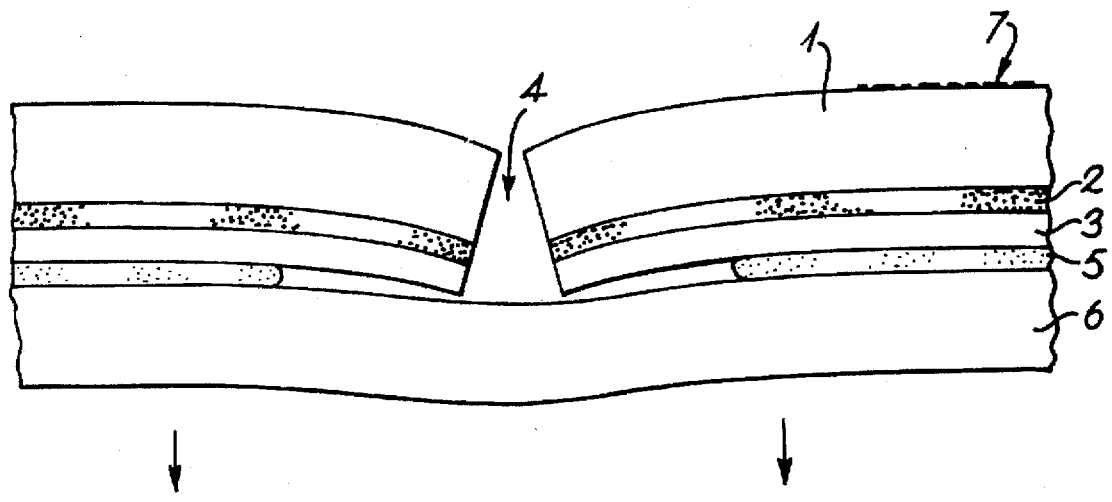
FIGS. 5 and 6 show two version of a pre-pecked stick-on patch for applying to a 1 cm square hole in a product package.
Figure 6:
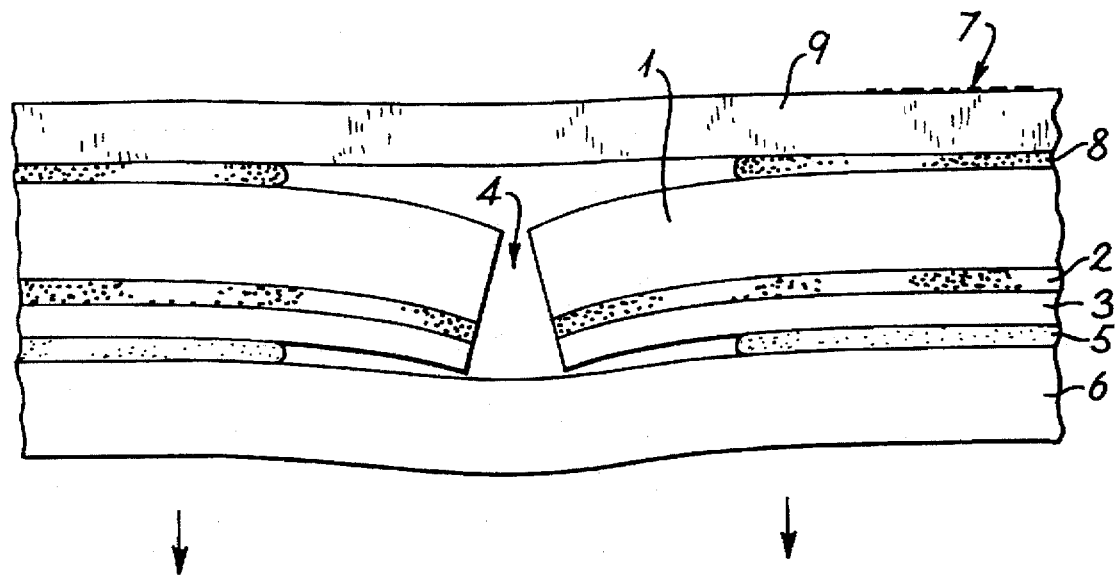

FIGS. 5 and 6 show two versions of a pre-pecked stick-on patch for applying to a 1 $cm^2$ hole in a product package.

In FIG. 5, a bilayer material according to the invention consists of 36 micron polyethylene 1 stuck via an acrylic adhesive 2 (8 microns thick when dry) to a 12 micron polyethylene terephthalate layer 3. A passage, H-shaped in plan, was previously formed at 4 by a press knife. The material is mounted via a layer 5 of pressure-sensitive adhesive on a peel-off strip of paper 6. The layer 5 is applied in such a way as to avoid the passage 4 and therefore not to impede its opening. As the temperature rises, the material will tend to curl as shown, into the peel-off paper, and thus the edges round the hole tend to be protected by the peel-off paper 6. In use, a vegetable package or the like, completely wrapped but for a 1 $cm^2$ hole, is placed with the hole under the bilayer material. The paper 6 is removed and the material applied (in the direction of the arrows) about the hole, sticking via the exposed adhesive 5. A bar code 7 and/or other information is printed (before or afterwards), and the package is ready for sale or for distribution in the catering trade.

In FIG. 6, the same reference numerals are used for the same parts as in FIG. 5, and the mode of use is also the same. However, the polyethylene 1 of FIG. 6 is not printed, but on its upper side is applied a layer of adhesive 8, in the same pattern (avoiding the passage 4) as the adhesive 5. The adhesive 8 is used to receive a continuous microporous film 9, itself printed with the bar code 7.

The microporous film 9 has a two-fold function. It inhibits the passage 4 in the bilayer material from opening upwards (as drawn) in the event of temperature excursions below the lie-flat temperature, and it reduces possible ingress of dirt and micro-organisms into the package. The pore density and pore size of the film 9 would be selected by the designer according to the diffusivity and the smallest likely contaminating organism appropriate to the produce being packaged.

In certain applications, it will not matter if the holes enlarge below the lie-flat (set point) temperature, in which case neither expedient (oblique cuts, backing flaps or films) need be used. That is, on cooling to around −2° C., many respiring products meet trouble because they freeze and irreparably damage their cell walls (→mushy when thawed). The enlarging of apertures as temperature falls is but a minor irritant to an already spoilt product. On the other hand, many other respiring products can be put into deep-freeze storage without blanching (needed sometimes to deactivate enzymes slightly active even at −20° C.); for those, even at −20° C. a low-$O_2$ atmosphere is desirable for very long term storage and thus, for those, the oblique cut or backing flap or other expedient should be used to prevent the holes from opening below the set point. It would be conceivable for some applications to use oblique cuts or backing flaps to allow a hole to open during downward temperature excursions and not upwards excursions.

It will be readily appreciated that, with no or minimal modification, these materials can be used for medical dressings (e.g. for burns), ventilation control other than for foodstuffs, (if metal-filled) temperature-dependent radiation absorbers or reflectors, dosage release (e.g. of deodorant), variable vapour barriers (e.g. vapour transmission control in shoes and clothes), thermal valves such as for appropriately permeable boil-in-bag or microwavable sachets, and as the female fabric of a two-fabric temperature-dependent attachment system. Another possibility is that on temperature change, the opening holes can reveal a backing colour or message appropriate to the temperature (e.g. "Frost", on a roadside sign exploiting negative temperature excursions from a 0° C. lie-flat temperature and with prevention of opening as temperature rises above 0° C. The FIGS. 1 to 4 version may be used as a temperature-dependent friction material.

Other lie-flat temperatures (i.e. slits lying flat, apertures at their minimum opening) may be useful in various applications, e.g. −5° C. A very high lie-flat temperature, e.g. 30° C. or 40° C., could be used for perforated incident-sunshine-activated sunblinds or tropical shading, the slits opening only on downward temperature excursions and inhibited on upward temperature excursions.

We claim:

1. A wrappable packaging material sufficiently flexible for use as a wrapping and asymmetrically laminated from at least two plastic layers disposed adjacent to each other and having different coefficients of thermal expansion, the material having a non-straight slit, wherein the slit forms a passage through the plastic layers, which passage varies in size with temperature, at least over a certain temperature range, at a range greater than the thermal coefficient of expansion of the plastic layers.

2. A wrappable packaging material according to claim 1, wherein the slit has a form of a plurality of slots radiating from a junction.

3. A wrappable packaging material according to claim 2, wherein the junction is an aperture.

4. A wrappable packaging material according to claim 2, wherein an angle between at least one pair of adjacent slots is at most 90°.

5. A wrappable packaging material according to claim 1, whose gas permeability increases at least threefold form 5° C. to 20° C.

6. A wrappable packaging material according to claim 1, wherein a temperature at which the material tends to lie flat is in a range 0° C. to 20° C.

7. A wrappable packaging material according to claim 1, wherein the slit is formed by a laser.

8. A wrappable packaging material according to claim 1, wherein the layers are dimensionally inert to moisture.

9. A wrappable packaging material according to claim 8, wherein at least one of the layers is hydrophobic.

10. A wrappable packaging material according to claim 1, wherein a first of the layers is selected from the group consisting of polyester, polyamide, cellulose, and polyethylene terephthalate.

11. A wrappable packaging material according to claim 1, wherein a second of the layers is selected from the group consisting of polyolefin and ethyl vinyl acetate plastic.

12. A wrappable packaging material according to claim 1, with means to inhibit passage through the slit when a temperature deviates in one sense from a reference temperature.

13. A wrappable packaging material according to claim 12, wherein said means comprises a backing flap.

14. A wrappable packaging material according to claim 12, wherein said means consists in that the slit is obliquely cut.

15. A wrappable packaging material according to claim 1, wherein thicknesses of at least some of the layers have a thickness in at least approximate proportion to an inverse cube root of their respective Young's moduli.

16. A wrapper packaging material according to claim 1, further comprising a metal foil layer in contacting relation with one of the plastic layers.

17. A container comprising the wrappable packaging material according to claim 1.

18. A method of packaging edible produce, comprising the step of wrapping a portion of the produce in the wrappable packaging material according to claim 1.

19. A container according to claim 17, wherein the wrappable packaging material includes means for containing produce.

20. A container according to claim 17, wherein the wrappable packaging material is microwaveable.

21. A wrappable packaging material according to claim 11, wherein the polyolefin layer is metalized.

22. A method of packaging edible produce according to claim 18, wherein the entirety of the produce is wrapped in said wrappable packaging material.

23. A container according to claim 17, wherein the wrappable packaging material is boilable.

24. A wrappable packaging material according to claim 1, wherein the layers are substantially transparent.

25. A packaging material asymmetrically laminated from at least two plastic layers disposed adjacent to each other and having different coefficients of thermal expansion, the material having a non-straight slit, wherein thicknesses of the layers are in at least approximate proportion to an inverse cube root of their respective Young's moduli, and wherein the slit forms a passage through the plastic layers, which passage varies in size with temperature, at least over a certain temperature range, at a rate greater than the thermal coefficients of expansion of the plastic layers.

* * * * *